United States Patent [19]

Uno et al.

[11] 4,172,896
[45] Oct. 30, 1979

[54] METHANE-SULFONAMIDE DERIVATIVES, THE PREPARATION THEREOF AND COMPOSITION COMPRISING THE SAME

[75] Inventors: Hitoshi Uno, Takatsuki; Mikio Kurokawa, Kobe; Yoshinobu Masuda, Hirakata, all of Japan

[73] Assignee: Dainippon Pharmaceutical Co., Ltd., Osaka, Japan

[21] Appl. No.: 912,857

[22] Filed: Jun. 5, 1978

[51] Int. Cl.$^2$ .................... A61K 31/42; C07D 261/20; C07D 263/56
[52] U.S. Cl. .................................. 424/272; 548/217; 548/241
[58] Field of Search .................... 260/307 D, 307 DA; 424/272

[56] References Cited

U.S. PATENT DOCUMENTS 3,833,608  9/1974  Rooney et al. ............. 260/326.12 R

OTHER PUBLICATIONS

Noller—"Chemistry of Organic Compounds"—W. B. Saunders Company—(1965), pp. 314–315.

Primary Examiner—Raymond V. Rush
Attorney, Agent, or Firm—Stevens, Davis, Miller & Mosher

[57] ABSTRACT

Methane-sulfonamide derivatives of the formula:

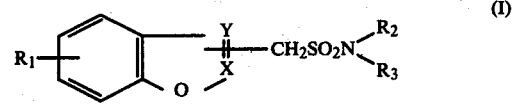

(I)

wherein $R_1$ is hydrogen or a halogen atom, $R_2$ and $R_3$ are the same or different and are each hydrogen or a straight or branched alkyl having 1 to 3 carbon atoms, and one of X and Y is a carbon atom and another is a nitrogen atom, provided that the group: $-CH_2SO_2NR_2R_3$ is bonded to the carbon atom of either of X and Y, and an alkali metal salt thereof, and a process for the preparation of said methane-sulfonamide derivatives. Said compounds have an excellent anticonvulsant activity and are useful as anticonvulsants for controlling convulsions and seizures in patients with epilepsy.

24 Claims, No Drawings

METHANE-SULFONAMIDE DERIVATIVES, THE PREPARATION THEREOF AND COMPOSITION COMPRISING THE SAME

The present invention relates to novel methane-sulfonamide derivatives, more particularly, to compounds of the formula:

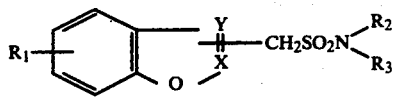

wherein $R_1$ is hydrogen or a halogen atom, $R_2$ and $R_3$ are the same or different and are each hydrogen or an alkyl having 1 to 3 carbon atoms, and one of X and Y is a carbon atom and another is a nitrogen atom, provided that the group: —$CH_2SO_2NR_2R_3$ is bonded to the carbon atom of either of X and Y, and an alkali metal salt thereof when either one or both of $R_2$ and $R_3$ are hydrogen atoms, and further relates to a process for the preparation of said methane-sulfonamide derivatives and also to a pharmaceutical composition containing said compounds as the essential active ingredient.

The term "halogen atom" denotes fluorine, chlorine and bromine atoms, and "alkyl" denotes a straight or branched alkyl having 1 to 3 carbon atoms, such as methyl, ethyl, propyl and isopropyl. "Alkali metal salt" includes sodium salt and potassium salt.

The compounds of the formula (I) include the following two types of compounds:

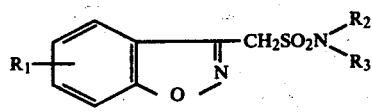

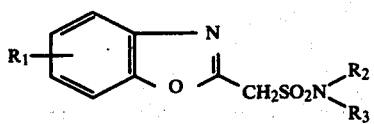

In the course of intensive studies on sulfamoyl-alkyl derivatives of various benzazoles, the present inventors have found that when sulfamoylmethyl group is introduced at the 3-position of 1,2-benzisoxazoles or at the 2-position of benzoxazoles, the resulting compounds show an excellent anticonvulsant activity.

Although some 3-sulfamoylmethylindole derivatives are disclosed in U.S. Pat. No. 3,833,608, the compounds of the formula (I) in the present invention are clearly different from these indole derivatives disclosed in the U.S. patent in the chemical structure and also in the pharmacological properties.

It is an object of the present invention to provide novel methane-sulfonamide derivatives and their alkali metal salts having an excellent anticonvulsant activity.

Another object of the invention is to provide a process for the preparation of the methane-sulfonamide derivatives and their alkali metal salts.

A further object of the invention is to provide a method of controlling convulsions and seizures in patients with epilepsy which comprises administering an effective amount of the methane-sulfonamide derivatives or their alkali metal salts.

A still further object of the invention is to provide a pharmaceutical composition comprising the methane-sulfonamide derivatives or their alkali metal salts as an active ingredient.

These and other objects will be apparent from the description hereinafter.

Preferred compounds of the present invention are the compounds of the formula (I) wherein $R_1$ is hydrogen or 5- or 6-halogen atom and $R_2$ and $R_3$ are the same or different and are each hydrogen or methyl. Particularly preferred compounds are the compounds of the formula (I) wherein $R_1$ is hydrogen or 5- or 6-halogen and $R_2$ and $R_3$ are both hydrogen. Suitable examples are as follows, among of which the first three compounds are particularly suitable.

3-Sulfamoylmethyl-1,2-benzisoxazole
5-Fluoro-3-sulfamoylmethyl-1,2-benzisoxazole
2-Sulfamoylmethylbenzoxazole
5-Chloro-3-sulfamoylmethyl-1,2-benzisoxazole
5-Bromo-3-sulfamoylmethyl-1,2-benzisoxazole
6-Fluoro-3-sulfamoylmethyl-1,2-benzisoxazole The compounds of the formula (I) can be prepared by reacting a compound of the formula:

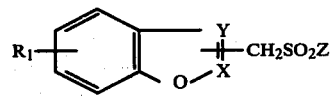

wherein $R_1$, X and Y are as defined above, and Z is a halogen atom (e.g. chlorine, bromine), with an amine of the formula:

wherein $R_2$ and $R_3$ are as defined above.

The reaction of the compound of the formula (II) with the amine of the formula (III) may be carried out in the absence of a solvent, but may preferably be carried out in the presence of an inert solvent. The inert solvent includes water, alcohols (e.g. ethanol, isopropanol), aromatic hydrocarbons (e.g. toluene, xylene), ethers (e.g. diethyl ether, tetrahydrofuran, dioxane), esters (e.g. ethyl acetate), or the like, which may be used alone or in a mixture of two or more thereof. Suitable solvents are ethers and esters.

The reaction is preferably carried out in the presence of a basic substance as a dehydrohalogenating agent. The basic substance includes alkali metal hydrogen carbonates (e.g. sodium hydrogen carbonate, potassium hydrogen carbonate), alkali metal carbonates (e.g. sodium carbonate, potassium carbonate), organic amines (e.g. triethylamine), or the like. Instead of using a specific basis substance, there may be used an excess amount of the amine of the formula (III) which acts as a reactant and also as a dehydrohalogenating agent.

The amine of the formula (III) is usually used in an amount of 1 to 4 moles to 1 mole of the compound of the formula (II), but may be used in a large excess amount. The reaction temperature is not critical, but the reaction is usually carried out at a temperature of from about 0° C. to about 35° C. The desired compound of the formula (I) can be isolated from the reaction mixture and purified in a conventional manner.

The starting compound of the formula (II) is preparing by reacting a halogenomethyl derivative of the formula:

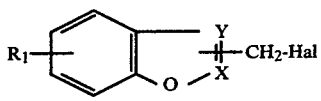

wherein $R_1$, X and Y are as defined above, and Hal is a halogen atom (e.g. chlorine, bromine, iodine), which is prepared by the similar process to that as disclosed in Chem. Pharm. Bull. (Tokyo), Vol. 24, page 632 (1976) and Belgian Pat. No. 624,463, with sodium sulfite in an inert solvent (e.g. aqueous methanol or aqueous ethanol) at a temperature of from 40° C. to 80° C. to give a sodium methanesulfonate of the formula:

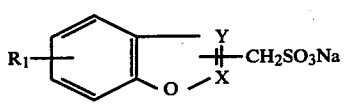

wherein $R_1$, X and Y are as defined above, and then reacting the resulting sodium methanesulfonate of the formula (V) with a halogenating agent (e.g. phosphorus oxychloride, phosphorus oxybromide).

The compound of the formula (I) wherein either one or both of $R_2$ and $R_3$ are hydrogen may be reacted with an alkali metal compound in a conventional manner to give an alkali metal salt of the compound of the formula (I). The alkali metal compound includes alkali metal hydroxide (e.g. sodium hydroxide, potassium hydroxide), alkali metal alcoholates (e.g. sodium ethylate), or the like.

The compounds of the formula (I) and their alkali metal salts of the present invention have an excellent anticonvulsant activity. The pharmacological test data of the representative compounds of the present invention are shown below together with the data of commercially available anticonvulsants.

(1) Anti-maximal electroshock seizure activity in mice

Male mice of STD-ddY strain were used. The test compounds were orally administered to the test animals (each group: 10 mice) in the form of a homogeneous suspension in a 0.5% tragacanth solution.

Maximal electroshock seizures (MES) were induced by the method of Swinyard [cf. J. Amer. Pharm. Assoc., Vol. 38, page 201 (1949)]. The animals were subjected to 60 Hz current of 25 mA for 0.2 second delivered through corneal electrodes after administration of the test compounds. Median effective dose (ED$_{50}$), i.e. the dose which prevents hindlimb tonic extensor components of seizures in 50% of animals, was calculated by the method of Litchfield and Wilcoxon [cf. J. Pharmacol. Exp. Ther., Vol. 96, page 99 (1947)].

The ED$_{50}$ at peak effect time of the compounds is shown in Tables 1a and 1b.

Table 1a

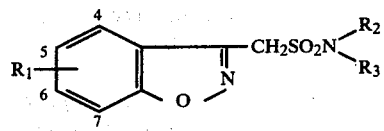

| No. | $R_1$ | $R_2$ | $R_3$ | ED$_{50}$ (mg/kg, p.o.) |
|---|---|---|---|---|
| 1 | H | H | H | 19.6 |
| 2 | H | H | CH$_3$ | 22.3 |
| 3 | H | H | C$_2$H$_5$ | 38.9 |
| 4 | H | H | CH(CH$_3$)$_2$ | 56.0 |
| 5 | H | CH$_3$ | CH$_3$ | 37.2 |
| 6 | 5-Cl | H | H | 14.2 |
| 7 | 5-Cl | H | CH$_3$ | ca. 20 |
| 8 | 5-Cl | H | C$_2$H$_5$ | 21.3 |
| 9 | 5-Cl | CH$_3$ | CH$_3$ | 56.2 |
| 10 | 5-F | H | H | 14.5 |
| 11 | 5-F | H | CH$_3$ | 34.5 |
| 12 | 5-F | H | C$_2$H$_5$ | 31.6 |
| 13 | 5-F | CH$_3$ | CH$_3$ | 32.0 |
| 14 | 5-Br | H | H | 13.5 |
| 15 | 5-Br | H | CH$_3$ | 15.0 |
| 16 | 5-Br | H | C$_2$H$_5$ | 18.3 |
| 17 | 5-Br | H | CH(CH$_3$)$_2$ | 22.3 |
| 18 | 6-F | H | H | 18.9 |

Table 1b

| No. | $R_1$ | $R_2$ | $R_3$ | ED$_{50}$ (mg/kg, p.o.) |
|---|---|---|---|---|
| 19 | H | H | H | 12.0 |
| 20 | H | H | CH$_3$ | 17.2 |
| 21 | H | CH$_3$ | CH$_3$ | 34.0 |
| 22 | H | H | (CH$_2$)$_2$CH$_3$ | 31.2 |
| 23 | 5-Cl | H | H | 30.3 |
| Diphenylhydantoin | | | | 7.6 |
| Carbamazepine | | | | 13.2 |
| Primidone | | | | 21.7 |
| Phenacemide | | | | 61.2 |

[Note]:
Diphenylhydantoin: 5,5-diphenyl-2,4-imidazolidinedione
Carbamazepine: 5H-dibenz[b,f]azepine-5-carboxamide
Primidone: 5-ethyl-5-phenylhexahydropyrimidine-4,6-dione
Phenacemide: phenylacetylurea The anti-MES activities of the compounds of this invention were more potent than that of phenacemide, while less than that of diphenylhydantoin. The activities of some compounds of this invention were almost equal to or more potent than those of carbamazepine and primidone.

(2) Effect on coordinated motor movements in mice

Mice trained to continue coordinated motor movements for 100 seconds or more on a rotarod apparatus (2.5 cm in diameter at 11 RPM) were used [J. Amer. Pharm. Assoc., Sci. Ed., Vol 46, page 208 (1957)]. Impairment of coordinated motor movements was defined as the inability of the animals to retain on the rotarod for a 100 second test period. After oral administration of the test compounds rotarod performance was tested at intervals of 1 hour for 6 hours. Median neurotoxic dose (NTD$_{50}$), i.e. the does which causes fall from rotarod in 50% of animals, was calculated by the method of Litchfield and Wilcoxon.

The NTD$_{50}$ at peak effect time of the test compounds is shown in Table 2. The protective indices (NTD$_{50}$/ED$_{50}$ of anti-MES) of the test compounds were calculated and are also shown in the same table.

Table 2

| Test compound[*1] | NTD$_{50}$ (mg/kg, p.o) | Protective index |
| --- | --- | --- |
| 1 | 292 (2)[*2] | 14.9 |
| 10 | 154 (2) | 10.6 |
| 19 | 168 (2) | 14.0 |
| Diphenylhydantoin | 72 (6) | 9.5 |
| Carbamazepine | 141 (1) | 10.7 |

[Note]:
[*1] The test compounds 1, 10 and 19 are as defined in Tables 1a and 1b.
[*2] Figures in parentheses represent peak effect time in hours.

Neurotoxic effects of the compounds of this invention were about one-half to about one-fourth as potent as that induced by diphenylhydantoin. The protective indices of the compounds of this invention were higher than that of diphenylhydantoin and were almost equal to or higher than that of carbamazepine. Therefore, the compounds of this invention have a wide separability of therapeutic effects from acute neurotoxic effects.

(3) Acute toxicity in mice

Male mice of STD-ddY strain weighing 20-22 g were used. The test compounds were orally administered to the test animals (each group: 10 mice) in the form of a homogeneous suspension in 0.5% tragacanth solution. The mortality was observed for 7 days. Median lethal dose (LD$_{50}$), i.e. the dose which causes death in 50% of animals, was calculated by Probit method.

The LD$_{50}$ of the test compound is shown in Table 3. The safety index (LD$_{50}$/ED$_{50}$ of anti-MES) of each compound was calculated and is also shown in the same table.

Table 3

| Test compound* | LD$_{50}$ (mg/kg, p.o) | Safety index |
| --- | --- | --- |
| 1 | 1829 | 93.3 |
| 10 | 1257 | 86.7 |
| 19 | ca.1800 | — |
| Diphenylhydantoin | 363 | 47.8 |
| Carbamazepine | 1700 | 129 |

[Note]:
*The test compounds 1, 10 and 19 are as defined in Tables 1a and 1b.

Acute lethal toxicities of the compounds of this invention were considerably weak compared with that of diphenylhydantoin. The safety indices of the compounds of this invention were about twice as high as that of diphenylhydantoin, while their indices were somewhat lower than that of carbamazepine. The compounds of this invention have large safety margins of therapeutic effects from acute lethal toxicities compared with diphenylhydantoin.

As is clear from the above test results, the compounds of the formula (I) and their alkali metal salts of the present invention have an excellent anticonvulsant activity and have a low toxicity, and hence, these compounds are useful as anticonvulsants for controlling convulsions and seizures in patients with epilepsy.

These compounds of the present invention can be administered by an oral, parenteral or intrarectal route. The dosage of these compounds may vary in accordance with the kinds of the compounds, the administration manner, the age of the patient and the degree of the therapeutic effect desired, but is usually in the range of 1 to 100 mg/kg/day, preferably 3 to 50 mg/kg/day, which may be administered at a time or in divided doses.

The compounds of the present invention are usually administered in the form of a pharmaceutical composition which contains them in admixture with a pharmaceutical carrier. The pharmaceutical composition may be in the dosage forms such as tablets, capsules, granules, fine granules, powders, syrups, suppositories, injections, or the like. These preparations can be prepared by conventional methods.

The carriers useful for these preparations include all organic or inorganic carrier materials which are usually used for the pharmaceutical preparations and are inert to the active ingredient. Examples of the carriers suitable for the preparation of tablets capsules, granules and fine granules are diluents such as lactose, starch, sucrose, D-mannitol, calcium sulfate, or microcrystalline cellulose; disintegrators such as sodium carboxymethylcellulose, modified starch, or calcium carboxymethylcellulose; binders such as methylcellulose, gelatin, acacia, ethylcellulose, hydroxypropylcellulose, or polyvinylpyrrolidone; lubricants such as light anhydrous silicic acid, magnesium stearate, talc, or hydrogenated oil; or the like. When formed into tablets, they may be coated in a conventional manner by using the conventional coating agents such as calcium phosphate, carnauba wax, hydroxypropyl methylcellulose, macrogol, hydroxypropyl methylphthalate, cellulose acetate phthalate, titanium dioxide, sorbitan fatty acid ester, or the like.

Examples of the carriers suitable for the preparation of syrups are sweetening agents such as sucrose, glucose, fructose, or D-sorbitol; suspending agents such as acacia, tragacanth, sodium carboxymethylcellulose, methylcellulose, sodium alginate, microcrystalline cellulose, or veegum; dispersing agents such as sorbitan fatty acid ester, sodium lauryl sulfate, or polysorbate 80; or the like. When formed into syrups, the conventional flavoring agents, aromatic substances, preservatives, or the like may optionally be added thereto. The syrups may be in the form of a dry syrup which is dissolved or suspended before use.

Examples of bases used for the preparation of suppositories are cacao butter, glycerin saturated fatty acid ester, glycerogelatin, macrogol, or the like. When formed into suppositories, the conventional surface active agents, preservatives or the like may optionally be admixed.

When formed into injections, the alkali metal salt of the compound is dissolved in distilled water for injection, to which may optionally be added the conventional solubilizers, buffering or pH adjusting agents, isotonic agents, preservatives and other suitable substances. The injections may be in the solid dry preparations which are dissolved before use.

These pharmaceutical compositions usually contain the compounds of the formula (I) or their alkali metal salts as the active ingredient in an amount of 0.5% by weight or more, preferably 10 to 70% by weight, based on the total weight of the composition. These compositions may optionally contain other therapeutically active compounds.

The present invention is illustrated by the following Examples, but is not limited thereto. In Examples, the compounds were identified by elementary analysis, mass spectrum, IR spectrum, NMR spectrum, or the like.

EXAMPLE 1

1,2-Benzisoxazole-3-methanesulfonyl chloride:

To a solution of 8.0 of 3-bromomethyl-1,2-benzisoxazole (m.p. 64°–66° C.) in 130 ml of methanol was added a solution of 8.1 g of sodium sulfite in 130 ml of water. The mixture was heated with stirring at 50° C. for 4 hours and concentrated under reduced pressure. The crystalline residue was dissolved in 250 ml of methanol with warming and the insoluble material was filtered off. The filtrate was concentrated under reduced pressure and the crystalline residue was washed with diethyl ether to give crude sodium 1,2-benzisoxazole-3-methanesulfonate (10.5 g).

To 100 ml of phosphorus oxychloride was added 10.5 g of the above-mentioned sodium salt and the mixture was heated under reflux for 3 hours. The excess of phosphorus oxychloride was distilled off under reduced pressure. The residue was dissolved in 200 ml of ethyl acetate and the removal of the insoluble material by filtration gave the solution of the desired product.

EXAMPLE 2

The following compounds were prepared in substantially the same manner as in Example 1:

5-Fluoro-1,2-benzisoxazole-3-methanesulfonyl chloride;

5-Chloro-1,2-benzisoxazole-3-methanesulfonyl chloride;

5-Bromo-1,2-benzisoxazole-3-methanesulfonyl chloride;

6-Fluoro-1,2-benzisoxazole-3-methanesulfonyl chloride.

EXAMPLE 3

3-Sulfamoylmethyl-1,2-benzisoxazole:

The solution of 1,2-benzisoxazole-3-methanesulfonyl chloride in ethyl acetate, which was prepared in Example 1, was cooled on an ice bath, saturated with dry ammonia gas, and allowed to stand at room temperature for one hour. After the removal of the insoluble material by filtration, the filtrate was concentrated to yield a crystalline solid, which was washed with a small amount of ethyl acetate and recrystallized from ethyl acetate to give the desired product (5.2 g), m.p. 160°–163° C.

EXAMPLE 4

5-Fluoro-3-sulfamoylmethyl-1,2-benzisoxazole:

Sixty six grams of sodium 5-fluoro-1,2-benzisoxazole-3-sulfonate, which was prepared in substantially the same manner as described in the first paragraph of Example 1, was dissolved in 500 ml of phosphorus oxychloride and the solution was heated under reflux for 4 hours. After the removal of the remaining phosphorus oxychloride by distillation, the residue was dissolved in 500 ml of benzene and then filtered. The filtrate was concentrated under reduced pressure and the residue was dissolved in 500 ml of diethyl ether. The resulting solution was saturated with dry ammonia gas under cooling on an ice bath and allowed to stand at room temperature for 30 minutes. The solvent was evaporated under reduced pressure and the residue was extracted with ethyl acetate. The ethyl acetate layer was concentrated to a volume of about 100 ml under reduced pressure. The crystalline precipitate was collected and washed with benzene to give the desired product (32 g), m.p. 182°–185° C.

EXAMPLE 5

Various compounds of the formula:

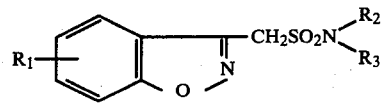

as listed in the following Table 4 were prepared in substantially the same manner as in Examples 3 and 4.

Table 4

| $R_1$ | $R_2$ | $R_3$ | Melting point (°C.) |
|---|---|---|---|
| H | H | $CH_3$ | 113–115 |
| H | H | $C_2H_5$ | 76–78 |
| H | H | $(CH_2)_2CH_3$ | 86–88 |
| H | H | $CH(CH_3)_2$ | 114–117 |
| H | $CH_3$ | $CH_3$ | 105–107 |
| 5-F | H | $CH_3$ | 141–144 |
| 5-F | H | $C_2H_5$ | 114–117 |
| 5-F | H | $CH(CH_3)_2$ | 127–130 |
| 5-F | $CH_3$ | $CH_3$ | 145–148 |
| 6-F | H | H | 187–190 |
| 5-Cl | H | H | 192–195 |
| 5-Cl | H | $CH_3$ | 148–151 |
| 5-Cl | H | $C_2H_5$ | 150–152 |
| 5-Cl | H | $CH(CH_3)_2$ | 114–116 |
| 5-Cl | $CH_3$ | $CH_3$ | 176–179 |
| 5-Br | H | H | 221–225 |
| 5-Br | H | $CH_3$ | 152–154 |
| 5-Br | H | $C_2H_5$ | 144–147 |
| 5-Br | H | $CH(CH_3)_2$ | 95–97 |
| 5-Br | $CH_3$ | $CH_3$ | 183–185 |

EXAMPLE 6

Benzoxazole-2-methanesulfonyl chloride:

To a solution of 3.0 g of 2-bromomethylbenzoxazole [prepared according to the procedures described in Belgian Pat. No. 624,463] in 40 ml of methanol was added a solution of 1.9 g of sodium sulfite in 40 ml of water. The mixture was heated with stirring at 60° C. for 6 hours and concentrated under reduced pressure to give crude sodium benzoxazole-2-methanesulfonate (4.5 g). To the sodium salt was added 15 ml of phosphorus oxychloride and the mixture was heated under reflux for one hour. The removal of the remaining phosphorus oxychloride by distillation under reduced pressure gave the desired product as an oil.

EXAMPLE 7

2-Sulfamoylmethylbenzoxazole:

The benzoxazole-2-methanesulfonyl chloride, which was prepared in Example 6, was dissolved in 100 ml of ethyl acetate, saturated with dry ammonia gas under cooling on an ice bath, and allowed to stand at room temperature for 30 minutes. Evaporation of the solvent under reduced pressure gave an oily residue, which was chromatographed on silica gel with 3% methanol-chloroform as eluent. The eluate was concentrated to dryness and the crystalline residue was recrystallized from ethyl acetate to give the desired product (0.4 g), m.p. 166°–169° C.

EXAMPLE 8

5-Chlorobenzoxazole-2-methanesulfonyl chloride was prepared in substantially the same manner as in Example 6.

EXAMPLE 9

Various compounds of the formula:

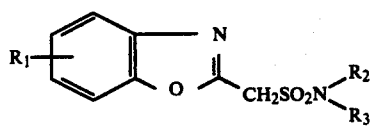

as listed in the following Table 5 were prepared in substantially the same manner as in Example 7.

Table 5

| $R_1$ | $R_2$ | $R_3$ | Melting point (°C.) |
| --- | --- | --- | --- |
| H | H | $CH_3$ | 139–142 |
| H | $CH_3$ | $CH_3$ | 109–111 |
| H | H | $(CH_2)_2CH_3$ | 146–149 |
| 5-Cl | H | H | 188–191 |

EXAMPLE 10

Sodium salt of 3-sulfamoylmethyl-1,2-benzisoxazole:

To a solution of 7.0 g of 3-sulfamoylmethyl-1,2-benzisoxazole in 300 ml of ethanol was added a solution of sodium ethylate which was prepared from 0.76 g of sodium and 40 ml of ethanol. The mixture was allowed to stand at room temperature for a while and evaporated to one-fifth of its original volume under reduced pressure. The concentrated solution was cooled and the crystalline precipitate was collected, washed with ethanol and dried to give the desired product (6.5 g), m.p. 225°–230° C. (decomposition).

EXAMPLE 11

The following compounds were prepared in substantially the same manner as in Example 10:

Sodium salt of 5-fluoro-3-sulfamoylmethyl-1,2-benzisoxazole, m.p. 240°–243° C. (decomposition);

Sodium salt of 2-sulfamoylmethylbenzoxazole, m.p. 265°–267° C. (decomposition).

EXAMPLE 12

|  | per 1,000 tablets |
| --- | --- |
| 3-Sulfamoylmethyl-1,2-benzisoxazole | 100 g |
| Lactose | 35 g |
| Corn starch | 17 g |
| Microcrystalline cellulose | 40 g |
| Polyvinylpyrrolidone | 6 g |
| Light anhydrous silicic acid | 1 g |
| Magnesium stearate | 1 g |

The above components were blended, granulated and made into tablets by a conventional method. 1,000 tablets each weighing 200 mg were formed.

EXAMPLE 13

| 3-Sulfamoylmethyl-1,2-benzisoxazole | 200 g |
| --- | --- |
| Lactose | 779 g |
| Hydroxypropylcellulose | 20 g |
| Light anhydrous silicic acid | 1 g |

The above components were blended and made into fine granules by a conventional method.

EXAMPLE 14

The same procedures as in Examples 12 and 13 were repeated except that 5-fluoro-3-sulfamoylmethyl-1,2-benzisoxazole or 2-sulfamoylmethylbenzoxazole was used instead of 3-sulfamoylmethyl-1,2-benzisoxazole. Thus, tablets and fine granules of each compound were prepared respectively.

What is claimed is:

1. A compound of the formula:

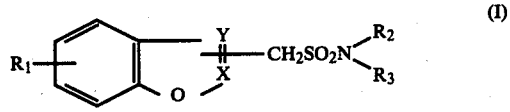

wherein $R_1$ is hydrogen or a halogen atom, $R_2$ and $R_3$ are the same or different and are each hydrogen or an alkyl having 1 to 3 carbon atoms, and one of X and Y is carbon atom and another is nitrogen atom, provided that the group:

—$CH_2SO_2NR_2R_3$ is bonded to the carbon atom of either of X and Y, or an alkali metal salt thereof.

2. A compound of the formula:

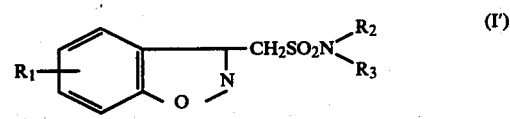

wherein $R_1$ is hydrogen or a halogen atom, and $R_2$ and $R_3$ are the same or different and are each hydrogen or an alkyl having 1 to 3 carbon atoms, or an alkali metal salt thereof.

3. A compound of the formula:

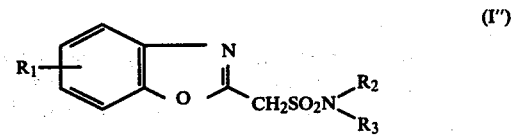

wherein $R_1$ is hydrogen or a halogen atom, and $R_2$ and $R_3$ are the same or different and are each hydrogen or an alkyl having 1 to 3 carbon atoms, or an alkali metal salt thereof.

4. A compound according to claim 1, 2 or 3, wherein $R_1$ is hydrogen or 5- or 6-halogen, or an alkali metal salt thereof.

5. A compound according to claim 4, wherein $R_2$ and $R_3$ are the same or different and are each hydrogen or methyl, or an alkali metal salt thereof.

6. A compound according to claim 5, wherein $R_2$ and $R_3$ are both hydrogen, or an alkali metal salt thereof.

7. 3-Sulfamoylmethyl-1,2-benzisoxazole or an alkali metal salt thereof.

8. 5-Fluoro-3-sulfamoylmethyl-1,2-benzisoxazole or an alkali metal salt thereof.

9. 5-Chloro-3-sulfamoylmethyl-1,2-benzisoxazole or an alkali metal salt thereof.

10. 5-Bromo-3-sulfamoylmethyl-1,2-benzisoxazole or an alkali metal salt thereof.

11. 6-Fluoro-3-sulfamoylmethyl-1,2-benzisoxazole or an alkali metal salt thereof.

12. 2-Sulfamoylmethylbenzoxazole or an alkali metal salt thereof.

13. A pharmaceutical composition comprising as an active ingredient a compound of the formula:

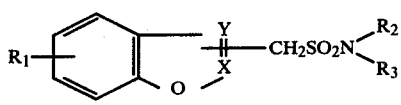

wherein $R_1$ is hydrogen or a halogen atom, $R_2$ and $R_3$ are the same or different and are each hydrogen or an alkyl group having 1 to 3 carbon atoms, and one of X and Y is carbon atom and another is nitrogen atom, provided that the group: $-CH_2SO_2NR_2R_3$ is bonded to the carbon atom of either of X and Y, or an alkali metal salt thereof and a pharmaceutically acceptable carrier.

14. A pharmaceutical composition according to claim 13, wherein the active ingredient is a compound of the formula:

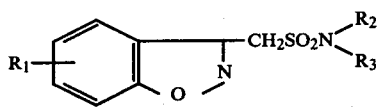

wherein $R_1$ is hydrogen or a halogen atom, and $R_2$ and $R_3$ are the same or different and are each hydrogen or an alkyl group having 1 to 3 carbon atoms, or an alkali metal salt thereof.

15. A pharmaceutical composition according to claim 13, wherein the active ingredient is a compound of the formula:

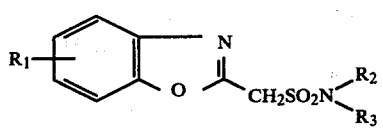

wherein $R_1$ is hydrogen or a halogen atom, and $R_2$ and $R_3$ are the same or different and are each hydrogen or an alkyl having 1 to 3 carbon atoms, or an alkali metal salt thereof.

16. A pharmaceutical composition according to claim 13 or 14, wherein the active ingredient is 3-sulfamoyl-methyl-1,2-benzisoxazole or an alkali metal salt thereof.

17. A pharmaceutical composition according to claim 13 or 14, wherein the active ingredient is 5-fluoro-3-sulfamoylmethyl-1,2-benzisoxazole or an alkali metal salt thereof.

18. A pharmaceutical composition according to claim 13 or 14, wherein the active ingredient is 2-sulfamoyl-methylbenzoxazole or an alkali metal salt thereof.

19. A method for controlling convulsions and seizures in patients with epilepsy which comprises administering an effective amount of a compound of the formula:

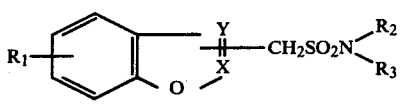

wherein $R_1$ is hydrogen or a halogen atom, $R_2$ and $R_3$ are the same or different and are each hydrogen or an alkyl having 1 to 3 carbon atoms, and one of X and Y is carbon atom and another is nitrogen atom, provided that the group: $-CH_2SO_2NR_2R_3$ is bonded to the carbon atom of either of X and Y, or an alkali metal salt thereof to said patients.

20. A method according to claim 19, wherein said compound is a compound of the formula:

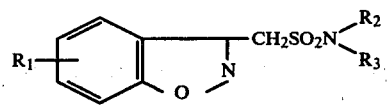

wherein $R_1$ is hydrogen or a halogen atom, and $R_2$ and $R_3$ are the same or different and are each hydrogen or an alkyl group having 1 to 3 carbon atoms, or an alkali metal salt thereof.

21. A method according to claim 19, wherein said compound is a compound of the formula:

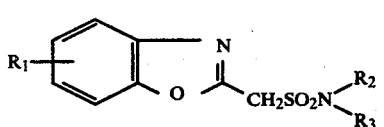

wherein $R_1$ is hydrogen or a halogen atom, and $R_2$ and $R_3$ are the same or different and are each hydrogen or an alkyl group having 1 to 3 carbon atoms, or an alkali metal salt thereof.

22. A method according to claim 19 or 20, wherein said compound is 3-sulfamoylmethyl-1,2-benzisoxazole or an alkali metal salt thereof.

23. A method according to claim 19 or 20, wherein said compound is 5-fluoro-3-sulfamoylmethyl-1,2-benzisoxazole or an alkali metal salt thereof.

24. A method according to claim 19 or 21, wherein said compound is 2-sulfamoylmethylbenzoxazole or an alkali metal salt thereof.

* * * * *

UNITED STATES PATENT AND TRADEMARK OFFICE
CERTIFICATE OF CORRECTION

PATENT NO. : 4,172,896
DATED : October 30, 1979
INVENTOR(S) : Hitoshi Uno et al

It is certified that error appears in the above-identified patent and that said Letters Patent are hereby corrected as shown below:

In col. 2, line 58, "basis" should be --basic--.

In col. 3, line 2, "ing" should be --ed--.

In col. 7, line 4, after "8.0" there should be --g--.

In Claim 2, line 2; Claim 14, line 4; and Claim 20, line 3, the formula should read as follows:

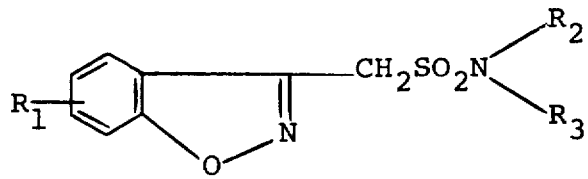

In Claim 18, line 2, "14" should be --15--.

Signed and Sealed this

Eighth Day of April 1980

[SEAL]

Attest:

SIDNEY A. DIAMOND

Attesting Officer     Commissioner of Patents and Trademarks